(12) United States Patent
Kawasumi et al.

(10) Patent No.: US 6,407,113 B1
(45) Date of Patent: Jun. 18, 2002

(54) MEDICAMENT FOR TREATMENT OF DIASTOLIC DYSFUNCTION

(75) Inventors: Hisashi Kawasumi; Yuji Abe; Naoya Satoh; Yoshimi Kitada, all of Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/969,649

(22) Filed: Oct. 4, 2001

Related U.S. Application Data

(63) Continuation of application No. 09/622,025, filed as application No. PCT/JP99/00562 on Feb. 10, 1999, now abandoned.

(30) Foreign Application Priority Data

Feb. 12, 1998 (JP) .............................................. 10-29678

(51) Int. Cl.[7] ............................................... A61K 31/495
(52) U.S. Cl. .................................................. 514/255.03
(58) Field of Search ...................................... 514/255.03

(56) References Cited

FOREIGN PATENT DOCUMENTS

| JP | 03-007263 | 1/1991 |
| JP | 04-139127 | 5/1992 |
| JP | 09-221479 | 8/1997 |
| JP | 10-298077 | 11/1998 |

*Primary Examiner*—Raymond Henley, III
(74) *Attorney, Agent, or Firm*—Wenderoth, Lind & Ponack, L.L.P.

(57) ABSTRACT

A medicament for treating or preventing diastolic dysfunction, comprising 2-(1-piperazinyl)-5-methylbenzenesulfonic acid derivative or its salt, or hydrate or solvate thereof as an active ingredient.

5 Claims, 4 Drawing Sheets

Results are shown as Mean Value + Standard Error
*P < 0.05; **P < 0.01 v.s. Control Group
(After repeated two-way ANOVA, determined by comparison using t-test)

Results are shown as Mean Value + Standard Error
*P < 0.05 (repeated ANOVA)

Results are shown as Mean Value + Standard Error
: p < 0.01 (paired t-test)
*: P < 0.05 v.s. Control (Dunnett Statistics)

MEDICAMENT FOR TREATMENT OF DIASTOLIC DYSFUNCTION

This application is a 53(b) continuation application of Ser. No. 09/622,025 filed Sep. 12, 2000, now abandoned, which is a 371 application of PCT/JP99/00562 filed Feb. 10, 1999.

FIELD OF THE INVENTION

The present invention relates to a medicament for treatment or prevention of diastolic dysfunction, particularly to those containing 2-(1-piperazinyl)-5-methylbenzenesulfonic acid derivative or its salt, or hydrate or solvate thereof as the active ingredient.

BACKGROUND OF THE INVENTION

The heart is one of the most important organs in organisms that serves as a pump for propelling blood into and through the arteries. It has two functions: diastolic and systolic functions. In the normal heart, the ventricular chambers are actively filled with the blood returned from the veious system during a diastole. In contrast, the blood filling the ventricular chamber will be ejected through aorta, against the pressure gradient, into systemic circulation during a systole.

On the other hand, cardiac dysfunction in diseased hearts may reduce cardiac output, resulting in insufficient systemic circulation. Although a living body may try to maintain these functions to some extent, by its compensatory mechanism, continued cardiac dysfunction could result in heart failure at least.

Conventionally, "heart (cardiac) failure" has often been regarded to be the same as "systolic dysfunction". In fact, however, it has been reported that as much as 40% of patients exhibiting "heart failure" had normal systolic function assessed by ejection fractions. Moreover, it has also been reported that 20% or more of patients with apparent "systolic dysfunction" exhibited no "heart failure" (Pouleur H. et al.: Focus on diastolic dysfunction: a new approach to heart failure therapy. Br. J. Clin. Pharmacol. 28: 41s, 1989). Recently, it has been accepted that diastolic dysfunction, insufficient relation of the left ventricle, is intimately associated with heart failure.

The more the concept and importance of diastolic dysfunction, in addition to systolic dysfunction, have been recognized for the understanding of pathophysiology of cardiac functions, the more the role of diastole dysfunction in pathophysiology of heart failure has been focused on.

Taken these into consideration, ACC(American College of Cardiology)/AHA(American Heart Association) Task Force (U.S.A.) stated, in "ACC/AHA Task Force Report; Guidelines for the Evaluation and Management of Heart Failure. Circulation. 92:2764–2784, 1995", that heart failure caused by diastolic dysfunction should be distinguished from one caused by systolic dysfunction by using Doppler-two-dimensional echocardiography or radionuclide imaging, or by cardiac catheterization, that it is preferable to treat heart failure patients distinctively depending on their cardiac function, systolic dysfunction or diastolic dysfunction.

In fact, however, there is no medical therapy that is effective for treatment of diastolic dysfunction by direct effects on cardiac muscles (Katz AM: Interplay between inotropic effects of cyclic adenosine monophosphate on the myocardial cell. Circulation (Suppl) 82: 1, 1990).

Diastolic dysfunction can be found not only in patients with heart failure but also in those with cardiac dysfunction induced by various causes such as hypertrophy induced by pressure overload and volume overload, sepsis, systemic shock, post-ischemic myocardium, idiopathic cardiomyopathy and diabetic cardiomyopathy.

Clinically, diastolic dysfunction has been recognized as important issue in ICU patients with cardiogenic or non-cardiogenic acute circulatory failure.

Recently, as the clinical importance of diastolic dysfunction has become more apparent and commonly understood, much attention has been paid to the hypothesis that the abnormal $Ca^{2+}$ uptake by sarcoplasmic reticulum, an organella in cardiac myocytes, commonly plays the main role in pathophysiology of "diastolic dysfunction".

In short, contraction and relaxation of cardiac muscle are dependent on cytosolic free $Ca^{2+}$ concentration. The $Ca^{2+}$ released from sarcoplasmic reticulum into cytoplasma during a systole is uptaken by the sarcoplasmic reticulum during a diastole. In diseased hearts, the $Ca^{2+}$ uptake ability is reduced, resulting in higher level of intracellular $Ca^{2+}$ during a diastole. $Ca^{2+}$ uptake into sarcoplasmic reticulum is carried out by $Ca^{2+}$ pump referred to as $Ca^{2+}$-ATPase present on the membrane of endoplasmic reticulum. It has been reported that such reduction in $Ca^{2+}$ uptake ability is accompanied by reduction in $Ca^{2+}$-ATPase activity in various diseased hearts (Angel Zarain-Herzberg, Nasir Afzal, Vijayan Elimban and Naranjan S. Dhalla: Decreased expression of cardiac sarcoplasmic reticulum $Ca^{2+}$ pump ATPase in congestive heart failure due to myocardial infarction. Molecular and Cellular Biochemistry 163/164: 285–290, 1996, Ulrich Schmidt, Maria Carles, Roger H. Hajjar, Thomas G. DiSalvo, Marc J. Semigran, G. William Dec, Jagat Narula, Ban-An Khaw, JudithK. Gwathmey: Abnormal Sarcoplasmic Reticulum $Ca^{2+}$ Activity and Uptake in Human Heart Failure. J. Am. Coll. Cardiol. 27 (Suppl A): 56A, 1996, D. Lagadic-Gossmann, K. J. Buckler, K. Le Prigent and D. Feuvray: Altered $Ca^{2+}$ handling in ventricular myocytes isolated from diabetic rats. Am. J. Physiol. 270: H1529–H1537, 1996).

Now, "diastolic dysfunction" is regarded as pathophysiological conditions underlying heart diseased with reduced sarcoplasmic reticulum $Ca^{2+}$-ATPase as well as those that are not always categorized according to the conventional definition of heart disease.

Aminobenzenesulfonic acid derivatives are known to inhibit overaccumulation of intracellular calcium ions in the cardiac muscle or the vascular smooth muscle, i.e., inhibit excess influx of extracellular calcium ions in disease heart (Japanese Patent Application Laid-Open No. 3-7263). It has been disclosed that such compounds may be an effective agent for prevention or treatment of ischemic heart disease, heart failure, hypertension and arrhythmia by inhibiting or reducing myocardial damages or defects in cardiac excitation conducting system (Japanese Patent Application Laid-Open No. 3-7263 and Japanese Patent Application Laid-Open No. 4-139127). However, any of these publications neither suggested nor stated that 2-(1-piperazinyl)-5-methylbenzenesulfonic acid derivative or its salt, or hydrate or solvate thereof may be useful for prevention or treatment of abnormal intracellular $Ca^{2+}$ handling, which could not be improved by any conventional techniques described above, mainly characterized by reduction in $Ca^{2+}$ uptake ability of intracellular sarcoplasmic reticulum of myocardial cytoplasmic system, and may be useful for prevention or treatment of "diastolic dysfunction" in cardiac contraction/relaxation cycle due to such abnormal $Ca^{2+}$ handling.

DISCLOSURE OF THE INVENTION

The object of the present invention is to provide a medicament for treatment or prevention of diastolic dysfunction.

The present inventors found, after intense studies to solve the above-described problems, that any compounds selected from the group comprising of 2-(1-piperazinyl)-5-methylbenzenesulfonic acid derivative or its salt, or hydrate or solvate thereof may provide preferable effects, i.e. preventing or treating the reduction in $Ca^{2+}$ uptake ability of myocardial sarcoplasmic reticulum, suggesting that such compounds will improve diastolic function. Further, these compounds have been found to improve the myocardial motion as well. Based on these findings, the present inventors developed the present invention.

In summary, the present invention relates to a medicament for treatment or prevention of diastolic dysfunction, comprising 2-(1-piperazinyl)-5-methylbenzenesulfonic acid derivative or its salt, or hydrate or solvate thereof as the active ingredient.

Preferable examples of the present invention include a medicament for treatment or prevention of diastolic dysfunction, comprising 2-(1-piperazinyl)-5-methylbenzenesulforic acid derivative monohydrate as the active ingredient, particularly, (1) a medicament for treatment or prevention of diastolic dysfunction in patients with cardiogenic circulation failure comprising any of the active ingredients described above; and (2) a medicament for treatment or prevention of diastolic dysfunction in patients with non-cardiogenic circulation failure comprising any of the active ingredients described above.

Alternatively, another aspect of the present invention provides a method for treatment or prevention of reduction in $Ca^{2+}$ uptake ability of cardiac sarcoplasmic reticulum by administering any medicaments described above to mammalians; a method for improving diastolic dysfunction; a method for improving reduced myocardial motility by virtue of such improvement of myocardial diastolic dysfunction by administering any medicaments described above to mammalians; and use of 2-(1-piperazinyl)-5-methylbenzenesulfonic acid derivative or its salt, or hydrate or solvate thereof for preparing the above-described medicaments.

BEST MODES FOR CARRYING OUT THE INVENTION

Figure 1:
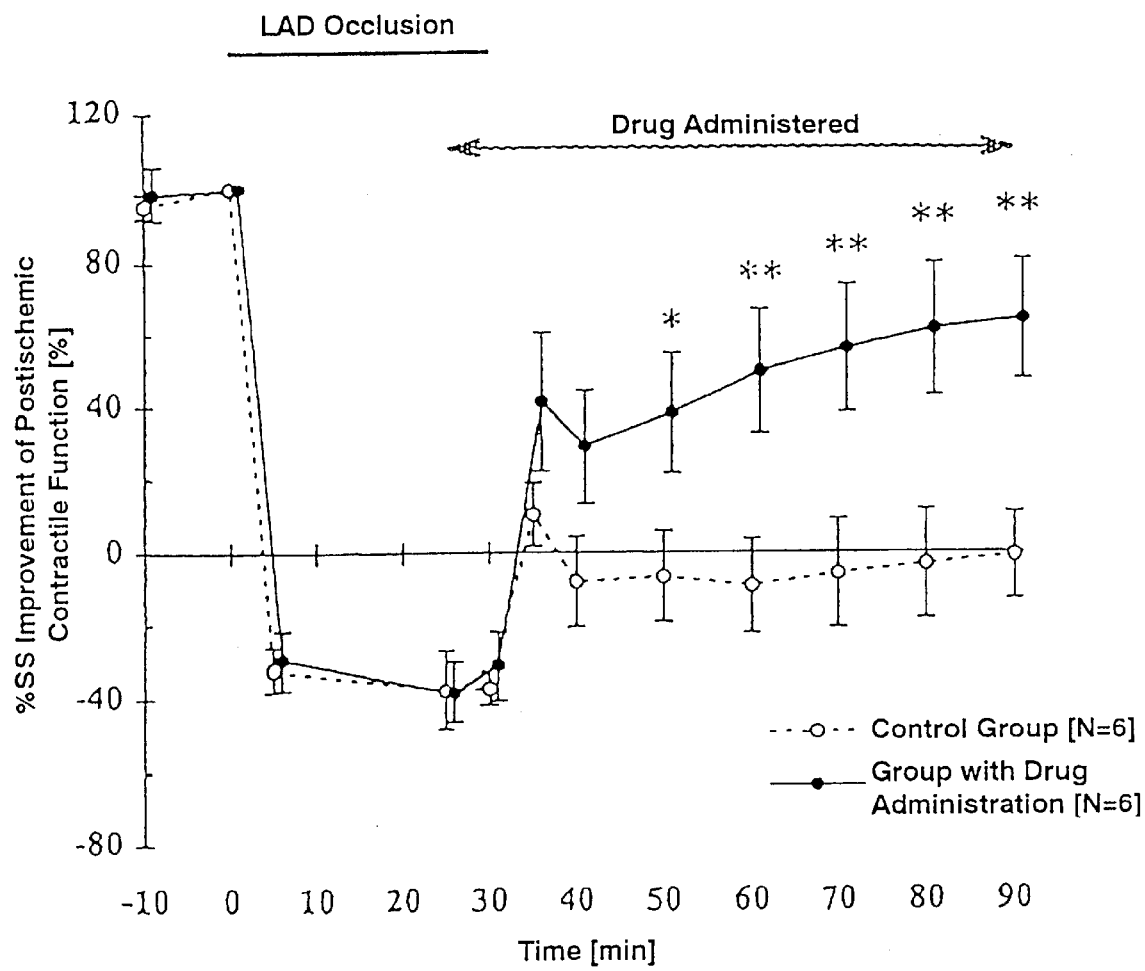
FIG. 1 is a diagram showing that the medicament of the present invention significantly improves the regional cardiac function (%SS) in the ischemic/reperfused myocardium.

The term "diastolic dysfunction" used herein refers to a disease condition with incomplete ventricular filling mainly due to relaxation failure during early diastole and/or reduced compliance during early to late diastole in the heart cycle of contraction and relaxation.

Clinical feature of patients who exhibit symptoms of diastolic dysfunction widely include asymptomatic disorder, respiratory difficulty, pulmonary edema, right ventricle failure, and exercise intolerance, whether cardiogenic or non-cardiogenic. Examples of cardiogenic heart disease are post-ischemic myocardium, diastolic heart failure, hypertrophy accompanying pressure overload or dosage overload, and idiopathic cardiomyopathy. Examples of non-cardiogenic are sepsis, systemic shock, diabetic cardiomyopathy. Preferred embodiment of the present invention is the treatment or prevention of diastolic dysfunction in cardiogenic diseases, particularly the treatment or prevention of diastolic dysfunction in the post-ischemic myocardium.

The medicaments of the present invention are expected to improve diastolic dysfunction by improving abnormal intracellular-handling $Ca^{2+}$, an important pathophysiological condition common in most diastolic dysfunction with various causative backgrounds. One of the active ingredients in the medicaments of the present invention, 2-(1-piperazinyl)-5-methylbenzenesulfonic acid derivative has the following formula:

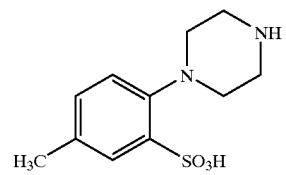

Examples of the above described salts of 2-(1-piperazinyl)-5-methylbenzenesulfonic acid derivatives are mineral salts, such as hydrochloride or sulfate, and organic acid salt such as acetate, malonate, fumarate, maleate, oxalate, lactate or metasulfate. Such compounds may be used as salt thereof, in free-form, or hydrate or solvate thereof as the active ingredient in the medicament of the present invention. Solvents which may be used for preparation of the above-described solvates include, for example, methanol, ethanol, isopropanol, acetone, ethyl acetate and methylenechloride. The most preferable active ingredient in the medicaments of the present invention is 2-(1-piperazinyl)-5-methylbenzenesulfonic acid derivative monohydrate.

2-(1-piperazinyl)-5-methylbenzenesulfonic acid derivative, the active ingredient in the medicaments of the present invention, per se is a known compound disclosed in Japanese Patent Application Laid-Open No. 3-7263 and Japanese Patent Application Laid-Open No. 4-139127 and can be easily synthesized according to, for example, the method described in Example 1 of Japanese Patent Application Laid-Open No. 3-7263. This compound is easily available for those skilled in the art. Salts of the above-described compound, or hydrates or solvates thereof may be synthesized according to any conventional procedure.

Although not being limited by any particular theory, the above-described 2-(1-piperazinyl)-5-methylbenzenesulfonic acid derivative is useful for preventing or treating the reduction in $Ca^{2+}$ uptake ability of cardiac sarcoplasmic reticulum, which may be the main cause for diastolic dysfunction in diseased hearts, as well as for improving reduced cardiac function. Accordingly, the medicaments of the present invention are useful for prevention and treatment of diastolic dysfunction.

Particularly, the medicaments of the present invention advantageously improve $Ca^{2+}$ uptake ability of sarcoplasmic reticulum in disease hearts (as described above) of experimental animal model prepared by ischemia and reperfusion, as well as improve cardiac functions. Accordingly, the medicaments of the present invention may be useful for treatment of diastolic dysfunction, for example, in the post-ischemic myocardium.

Alternatively, the medicaments of the present invention can be used for prevention and treatment of not only the ischemic/reperfused myocardium but also various diseases with similar pathophysiological background, such as diastolic heart failure, hypertrophy accompanying pressure overload or dosage overload, idiopathic cardiomyopathy, sepsis, systemic shock, and diabetic cardiomyopathy since they improve reduced sarcoplasmic reticulum $Ca^{2+}$ uptake ability in post-ischemic myocardium.

2-(1-piperazinyl)-5-methylbenzenesulfonic acid derivative or its salt, or a hydrate or solvate thereof, the active ingredients in the medicaments of the present invention, may be administered as a medicament per se to a patient. Preferably, however, they may be typically administered to a patient as a pharmaceutical composition which contains at least one of these active ingredients. Such pharmaceutical compositions include formulations for oral administration such as tablet, capsule, fine grain, powder, pill, troche, sublingual tablet or liquid, or those for parenteral administration such as injection, suppository, ointment or attachment.

Tablet or capsule-type formulation for oral administration may be typically presented in unit dose form and may be prepared by adding conventional pharmaceutical carrier such as binder, filler, diluent, tablet maker, lubricant, disintegrator, colorant, flavor and wetting agent. Tablet may be prepared according to any well-known procedure such as enteric coated preparation. For example, tablet may be prepared by using filler such as cellulose, mannitol or lactose; disintegrator such as starch, polyvinylpolypyrolidone, starch derivative or sodium starch glycolate; lubricant such as magnesium stearate; and wetting agent such as lauryl sodium sulfate.

Liquid formulation for oral administration may be presented as aqueous or oil suspension, solution, emulsion, syrup, elixir or other dry formulations which may be re-dissolved in water or any suitable solvent prior to use. Such liquid formulations may contain conventional additives including suspending agents such as sorbitol, syrup, methycellulose, gelatin and hydroxyethylcellulose carboxymethylcellulose, aluminum stearate gel or diet fat hydride; emulsifiers such as lecithin, sorbitan monooleate and gum arabic; non-aqueous solvent such as almond oil, purified coconut oil, oily ester (e.g., ester of glycerin), propylene glycole and ethyl alcohol (including diet oil); preservatives such as methyester, ethylester or propylester of p-hydroxybenzoic acid or sorbic acid; and optionally conventional flavors or colorants.

Formulation for oral administration may be prepared according to any well-known method in the art such as mixing, filling, or tablet-making. Alternatively, the active ingredient may be distributed in a formulation containing large amount of filler or other agents by using repeated mixing operations. Generally, formulations for parenteral administration may be presented as dosage formulation of liquid carrier-type which comprises the active ingredient (compound) and sterilized medium. Solution-type formulation for parenteral administration may be generally formed by dissolving such compound in a solvent, sterilized-filtering, and filling the solution in any suitable vial or ampoule which is then sealed. For higher stability, the compositions may be frozen prior to be filled in a vial, and then removed of water in vacuum. Suspension-type formulation for parenteral administration may be prepared substantially in the same manner as for solution-type formulation for parenteral administration. Preferably, it may be prepared by suspending such active ingredient in a medium and then sterilizing the suspension with, for example, ethylene oxide. Other additives such as surfactant or wetting agent may be added to the formulation in order to distribute the active ingredient uniformly.

The dosage of the above-described compound (the active ingredient) may be conveniently determined depending on the type of disease to be treated, symptoms of the disease, body-weight, age, sex or others conditions of the patient. Generally, such formulation may be orally administered to an adult at about 0.01 mg–1000 mg per day. Desirably, such dosage may be administered in single to several doses.

EXAMPLES

Synthesis 1: Preparation of 2-(1-Piperazinyl)-5-Methylbenzenesulfonic Acid Derivative Monohydrate According to the method described in Example 1 of Japanese Patent Application Laid-Open No. 3-7263, 2-fluoro-5-methylbenzene sulfonic acid (0.76 g) was reacted with piperazine (3.44 g) in the co-presence of cuprous iodide (0.76 g) and copper powder (0.26 g) in a sealed tube at 160° C. for 8 hours. Then, the reaction product was purified on silica gel column chromatography (eluent=chloroform: methanol: acetic acid=100: 100: 3) to give anhydrous crystal of 2-(1-piperazinyl)-5-methylbenzenesulfonic acid derivative (0.67 g, yield=65.0%).

The anhydrous crystal of 2-(1-piperazinyl)-5-methylbenzenesulfonic acid derivative (0.4506 g) and distilled water (1.35 ml) were added to a 5 ml flask, and stirred at 5° C. for 2 hours. Crystals were recovered from the suspension by suction filtration and then the residual crystals remaining in the flask were recovered by washing with filtrate. The crystals were combined and dried at 50° C., 90 mmHg for 3 hours to give white product, 2-(1-piperazinyl)-5-methylbenzenesulfonic acid derivative monohydrate (0.4485 g, yield 93.0%). This compound was verified as the monohydrate from the following results of elemental analysis.

Anal.: Theoretical value (monohydrate crystal): C: 48.16, H: 6.62, N: 10.21, S:11.69; Found: C: 48.16, H: 6.55, N: 10.09, S:11.87; (Reference): Theoretical value (anhydrate crystal): C: 51.54, H: 6.29, N: 10.93. S:12.51.

Hereinafter was used 2-(1-piperazinyl)-5-methylbenzenesulfonic acid derivative monohydrate as the medicament in Examples.

Example 1

Improvement of the Reduced Sarcoplasmic Reticulum $Ca^{2+}$-pumping ATPase Activity and Cardiac Function in Brief-ishcemic/reperfused Myocardium in Dogs The chest of mongrel dogs (adult, male and female) was opened under anesthesia with pentobarbital (30 mg/kg, i.v.) and a portion of the left coronary anterior descending (LAD) was dissected. A catheter-tip-pressure transducer (Millar;

MPC-500) was inserted from the left carotidartery into the left ventricle to determine the left ventricular pressure and its first differential value (dP/dt). A pair of crystal probes were mounted in the LAD region to determine changes in regional segment length. Diastolic segment length (EDL; threshold point of dP/dt) and systolic segment length (ESL; dP/dt(−) max point) were determined from the waveform of dP/dt, and the regional segment shortening (%SS) in the ischemic/reperfused myocardium was calculated as follows:

%SS=(EDL−ESL)/EDL×100.

After hemodynamic stability is established following operation, the dissected portion of LAD was occluded for 30 minutes and then reperfused for 1 hour. At the same time, the cardiac function (%SS) in the above-described ischemic/reperfused region was continuously monitored through-out the protocol.

The animals were randomly grouped into two groups, one consisting of animals to be administered with the medicament of the present invention (Drug administration group; N=6) and the other of control group (N-6). The dogs of drug administration group were intravenously administered with the medicament of the present invention (3 $\mu$g/kg) into the right femoral vein 5 minutes before reperfusion, followed by continuous infusion at 30 $\mu$g/kg/hr. Dogs of the control group were administered with the equal amount of saline.

After 1-hour reperfusion, their hearts were isolated and the myocardium in post-ischemic region and non-ischemic region of the left ventricles were collected from which the fractions having sarcoplasmic reticulum $Ca^{2+}$-ATPase activity were extracted to be subjected to protein assay (Bradford method) and stored at −80° C. The defrozen fractions were used to determine $Ca^{2+}$-ATPase activity. The activity was determined by measuring the amount of the generated inorganic phosphate (Pi) by colorimetry using phosphor/molybdic acid and malachite green ($\mu$moles Pi/mg protein/min).

The time-dependent recovery rates of regional cardiac function (%SS) in post-ischemic region relative to pre-ischemic value, for control group and drug administration group are shown in FIG. 1. Contractile function of myocardium after 30 minute-LAD occlusion followed by reperfusion was significantly reduced. Particularly, the reduced state was maintained for 1 hour in the control group. In drug administration group, regional cardiac function in post-reperfusion region was significantly improved when compared to that of the control group (time-course recovery rate for each group was analyzed by repeated two-way ANOVA and t-test was carried out at each time point after ischemia when a significant difference was present). Thus, it was demonstrated that the reduced cardiac function in the post-ischemic region of the myocardium after reperfusion will be improved by administration of the medicament of the present invention just prior to reperfusion.

Figure 2:
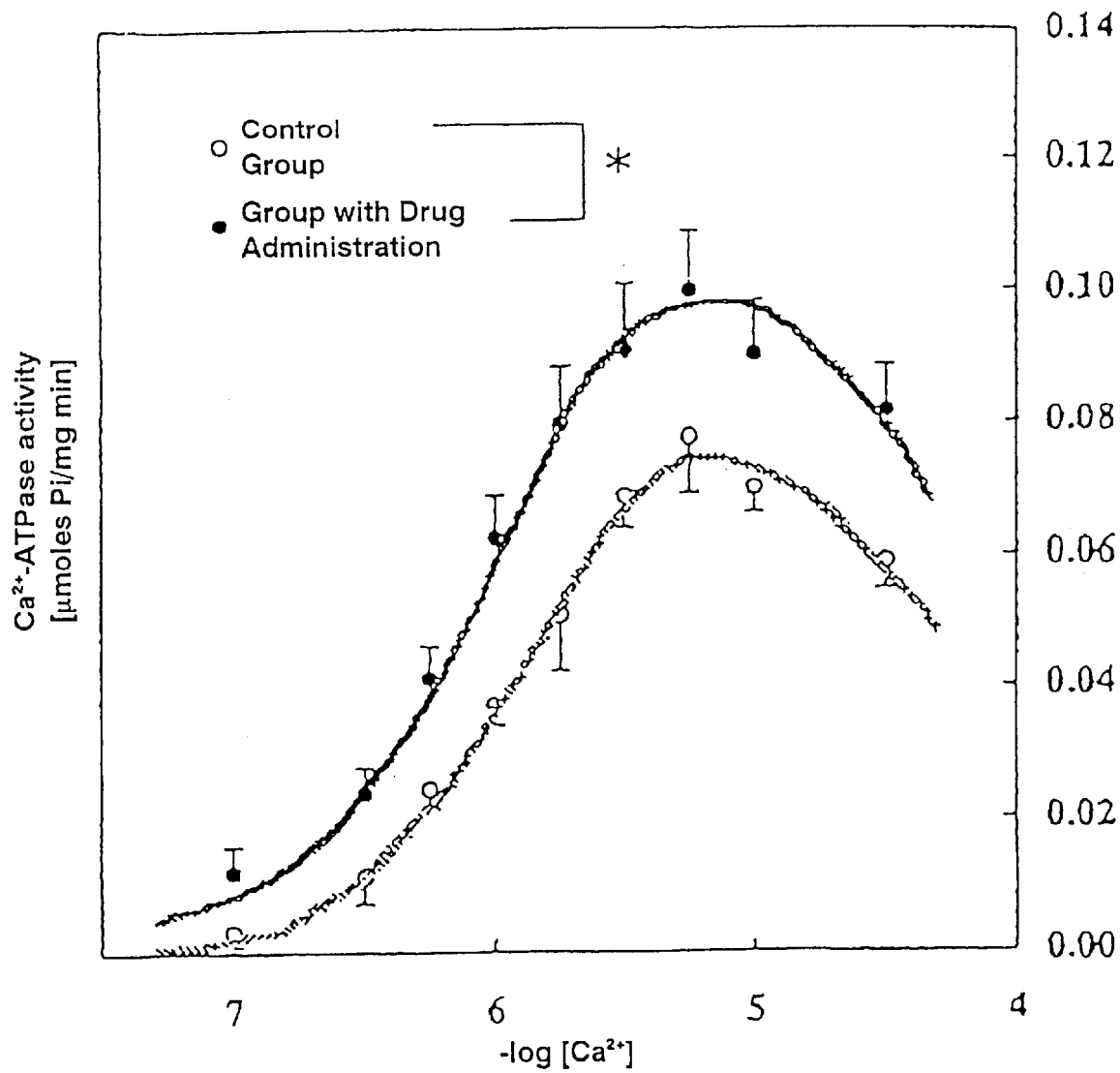
FIG. 2 is a diagram showing that the medicament of the present invention preventively improves the reduction in $Ca^{2+}$ uptake ability of the cardiac sarcoplasmic reticulum of the ischemic/reperfused myocardium in vivo.
Figure 3:
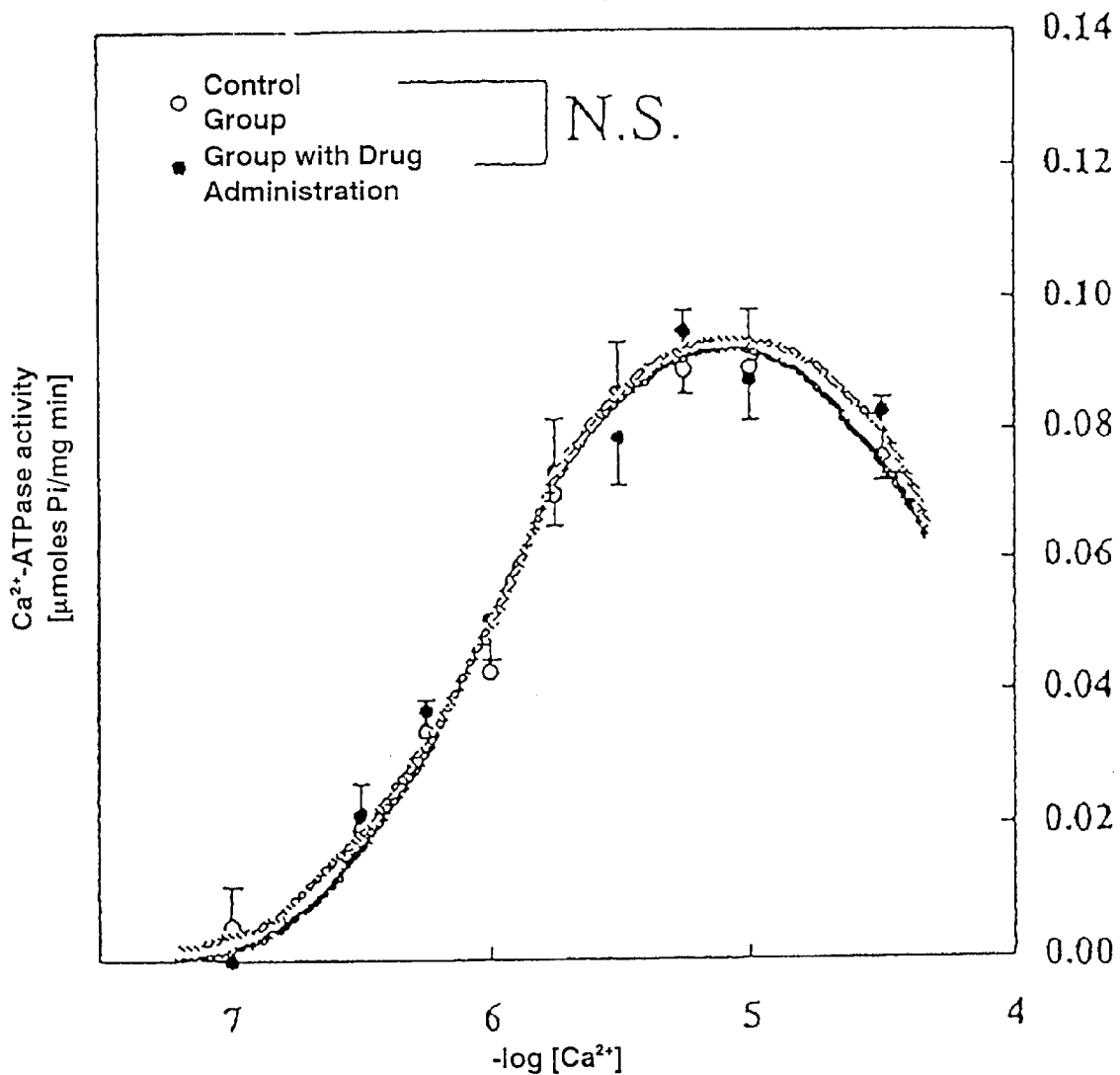
FIG. 3 is a diagram showing that the medicament of the present invention has little effect on $Ca^{2+}$ uptake ability in non-ischemic region

Next, results obtained from the $Ca^{2+}$-ATPase activity assay of the sarcoplasmic reticulum collected from each region are shown in FIGS. 2 and 3. The $Ca^{2+}$-ATPase activity of the sarcoplasmic reticulum showed $Ca^{2+}$-concentration-dependent patterns; the activity was increased at the threshold of 0.1 $\mu$M of $Ca^{2+}$ concentration and reached to the peak at about 10 $\mu$M. The ATPase activity was proved to be derived from the sarcoplasmic reticulum since the activity was completely inhibited by Thapsigargin (1 $\mu$M) which is known to be a specific inhibitor of the sarcoplasmic reticulum $Ca^{2+}$-ATPase.

In control group which was administered with saline, sarcoplasmic reticulum $Ca^{2+}$-ATPase activity of the myocardium collected from post-ischemic region was about 79% ([$Ca^{2+}$]=10 $\mu$M) of that of non-ischemic region.

Next, the activity was compared between the control group and drug administration group for each of post-ischemic region and non-ischemic region. In the post-ischemic region, $Ca^{2+}$-ATPase activity of the drug administration group was significantly higher than that of the control group (P<0.05 by repeated two-way ANOVA). For example, their activities at $Ca^{2+}$ concentration of 10 $\mu$M were 0.090±0.008 vs 0.070±0.004 [$\mu$mol Pi/mg min], respectively. Thus, it was proved that the reduced sarcoplasmic reticulum $Ca^{2+}$ uptake ability caused by ischemia and reperfusion is significantly improved by administering the medicament of the present invention just prior to reperfusion.

Further the $Ca^{2+}$-ATPase activity of sarcoplasmic reticulum from non-ischemic region was similarly compared between the two groups. The results showed no significant difference between the control group and drug administration group. For example, there was little difference between the two groups in the activity at $Ca^{2+}$ concentration of 10 $\mu$M (drug administration group: 0.088±0.006; control group: 0.089±0.009 [$\mu$mol Pi/mg min]).

The above results indicated that the medicament of the present invention may improve the reduction in sarcoplasmic reticulum $Ca^{2+}$-ATPase activity induced by ischemia/reperfusion while it has little effect on the ATPase activity in non-ischemic region. Further, the medicament of the present invention improved reduced cardiac function in ischemia/reperfusion region as well. Thus, the medicament of the present invention was proved to improve abnormal sarcoplasmic reticulum $Ca^{2+}$ uptake in the post-ischemic myocardium, as well as post-ischemic reduction in cardiac function.

Example 2

Direct Effect of the Agent on the Reduced $Ca^{2+}$-ATPase Activity

The $Ca^{2+}$-ATPase activity of the sarcoplasmic reticulum from both post-ischemic and non-ischemic regions of the left ventricle of dogs, in which LAD was occluded for 30 minutes followed by reperfusion for 30 minutes, was measured in the same manner as in Example 1. The direct effect of the medicament of the present invention on the sarcoplasmic reticulum was examined in vitro by determining the amount of inorganic phophorous generated during the reaction for 15 minutes, which was triggered by adding ATP to the reaction solution, with the preincubated medicament of the present invention at 37° C. for 5 minutes.

For each of post-ischemic region and non-ischemic region (N=6), three groups were tested; control group which was preincubated with $H_2O$, groups with low level dosage ($10^{-7}$ M of the medicament of the present invention was administered), and group with high level dosage ($10^{-6}$ M of the medicament of the present invention was administered)

The results showed that there was minor difference in sarcoplasmic reticulum $Ca^{2+}$-ATPase activity in non-ischemic region of groups with low level dosage and with high level dosages when compared to that of control group (control group: 0.057±0.003; group with low level dosage: 0.062±0.002; group with high level dosage: 0.060±0.003 [$\mu$mol Pi/mg min]), suggesting that the medicament of the present invention has little effect on the ATPase activity in the regions without ischemia/reperfusion.

Further, ATPase activity in post-ischemic region was significantly reduced when compared to that in non-ischemic myocardium (P<0.01, post-ischemic region control group vs non-ischemic region control group, with paired 1t O-test). Group with low level dosage showed tendency in recovery while group with high level dosage showed significantly higher value when compared to the reduced activity (P<0.05 vs control group, Dannett test). Activities were as follows: control group: 0.045±0.005; low concentration drug group: 0.057±0.003; high concentration drug group: 0.062±0.005 [μmol Pi/mg min].

Figure 4:
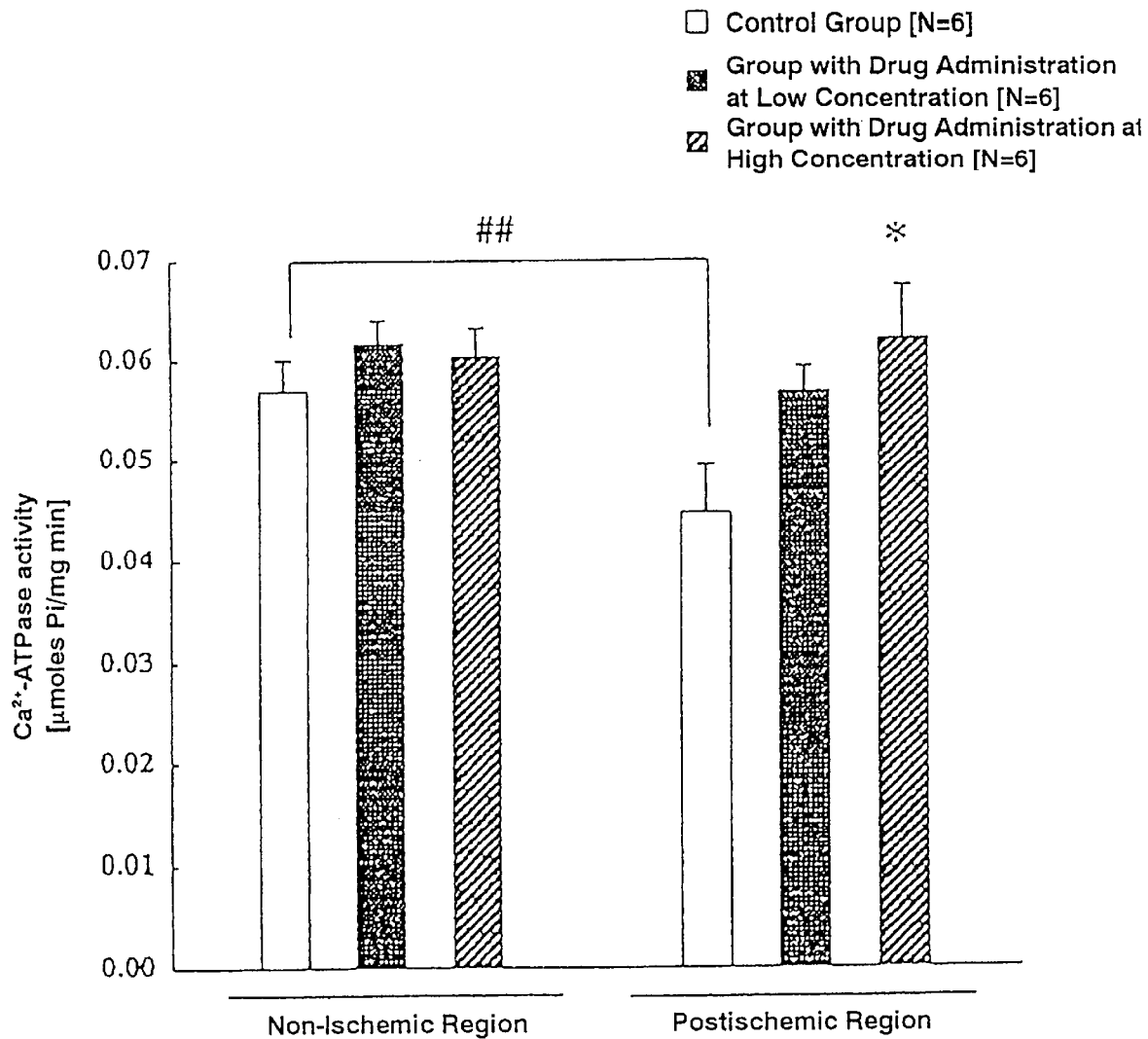
FIG. 4 is a diagram showing that the medicament of the present invention therapeutically improves the reduced $Ca^{2+}$ uptake ability of the sarcoplasmic reticulum of the ischemic/reperfused myocardium in vitro (left panel) while it has no effect on the activity in non-ischemic region in vitro.

Thus, it was suggested that the medicament of the present invention has minor effect on the $Ca^{2+}$ uptake ability of the sarcoplasmic reticulum in non-ischemic region while it has direct effect on cardiac sarcoplasmic reticulum in which the $Ca^{2+}$ uptake ability was reduced by ischemia/reperfusion, thereby improving the abnormality in vitro. The results are shown in FIG. 4.

INDUSTRIAL APPLICABILITY

The medicament of the present invention has a preventively effect on the: abnormal $Ca^{2+}$ uptake ability of the sarcoplasmic reticulum of post-ischemic myocardium in vivo, while therapeutically works on the abnormal $Ca^{2+}$-ATPase in vitro to improve such reduced $Ca^{2+}$-uptake ability. The medicament of the present invention also improved $Ca^{2+}$-uptake ability in the sarcoplasmic reticulum as well as improved cardiac function of post-ischemic myocardium in vivo.

Accordingly, the medicament of the present invention may be. useful for the treatment of not only post-ischemic myocardium but also various diseases caused by similar pathophysiology, such as diastolic heart failure, hypertrophy accompanying pressure overload or dosage overload, idiopathic cardiomyopathy, sepsis, systemic shock, and diabetic cardiomyopathy. Thus, the medicament of the present invention per se may be used to treat such diseases.

What is claimed is:

1. A method for treating or preventing the reduction in $Ca^{2+}$ uptake of cardiac sarcoplasmic reticulum, comprising administering an effective amount of 2-(1-piperazinyl)-5-methylbenzenesulfonic acid derivative or its salt, or hydrate or solvate thereof, to a patient in need thereof.

2. A method for treating or preventing-diastolic dysfunction, which comprises administering an effective amount of 2-(1-piperazinyl)-5-methylbenzenesulfonic acid derivative or its salt, or hydrate or solvate thereof, to a patient in need thereof.

3. A method for treating or preventing diastolic dysfunction, which comprises administering an effective amount of 2-(1-piperazinyl)-5-methylbenzenesulfonic acid derivative monohydrate to a patient in need thereof.

4. The method according to claim 2, wherein the patient has non-cardiogenic circulatory failure.

5. The method according to claim 3, wherein the patient has non-cardiogenic circulatory failure.

* * * * *